(12) United States Patent
Subramaniam et al.

(10) Patent No.: US 10,844,364 B2
(45) Date of Patent: Nov. 24, 2020

(54) NON-CONTACT SYSTEM FOR ACCELERATING WOUND HEALING USING AN ELECTROMAGNETIC COIL TO INDUCE AN ELECTRIC FIELD TRANSVERSE TO AN AXIS OF THE WOUND

(71) Applicant: Ohio State Innovation Foundation, Columbus, OH (US)

(72) Inventors: Vish Subramaniam, Westerville, OH (US); Joseph West, Richwood, OH (US); Emily Alkandry, Columbus, OH (US); Sashwati Roy, Columbus, OH (US); Chandan Sen, Upper Arlington, OH (US); Piya Ghatak, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 457 days.

(21) Appl. No.: 15/722,069

(22) Filed: Oct. 2, 2017

(65) Prior Publication Data
US 2018/0127737 A1 May 10, 2018

Related U.S. Application Data

(62) Division of application No. 14/766,011, filed as application No. PCT/US2014/014782 on Feb. 5, 2014, now Pat. No. 9,777,265.

(60) Provisional application No. 61/760,997, filed on Feb. 5, 2013.

(51) Int. Cl.
| | | |
|---|---|---|
| *C12N 13/00* | (2006.01) | |
| *A61N 2/00* | (2006.01) | |
| *A61N 2/02* | (2006.01) | |
| *C12M 1/42* | (2006.01) | |
| *C12M 1/34* | (2006.01) | |

(52) U.S. Cl.
CPC ............ *C12N 13/00* (2013.01); *A61N 2/004* (2013.01); *A61N 2/02* (2013.01); *C12M 35/02* (2013.01); *C12M 41/46* (2013.01)

(58) Field of Classification Search
CPC .............................. C12M 35/02; C12M 35/06
See application file for complete search history.

(56) References Cited

U.S. PATENT DOCUMENTS

| | | |
|---|---|---|
| 6,790,330 B2 | 9/2004 | Gascoyne et al. |
| 7,012,100 B1 | 3/2006 | Edwards et al. |
| 7,117,034 B2 | 10/2006 | Kronberg |
| 7,700,615 B2 | 4/2010 | Edwards et al. |

(Continued)

FOREIGN PATENT DOCUMENTS

WO     2011063458 A1     6/2011

OTHER PUBLICATIONS

Huo et al. "Noninvasive Electromagnetic Fields on Keratinocyte Growth and Migration." Journal of Surgical Research 162, pp. 299-307 (2010). (Year: 2010).*

(Continued)

*Primary Examiner* — William H. Beisner
(74) *Attorney, Agent, or Firm* — Standley Law Group LLP

(57) ABSTRACT

A system for accelerating the migration of cells by applying a time-varying magnetic field to induce eddy currents that promote electrotaxis (galvanotaxis) of cells. The system of the present invention accelerates the healing of wounds by electrotaxis of cells.

7 Claims, 9 Drawing Sheets

(56) References Cited

U.S. PATENT DOCUMENTS

| | | |
|---|---|---|
| 8,019,414 B2 | 9/2011 | Palti |
| 2004/0152067 A1 | 8/2004 | Wang et al. |
| 2006/0228795 A1* | 10/2006 | Parker .................. C12M 23/10 435/325 |
| 2006/0276858 A1 | 12/2006 | Palti |
| 2009/0018613 A1 | 1/2009 | Brighton |
| 2010/0298624 A1 | 11/2010 | Becker |
| 2011/0194979 A1 | 8/2011 | Chin et al. |
| 2012/0035457 A1 | 2/2012 | Subramaniam et al. |
| 2015/0353916 A1 | 12/2015 | Subramaniam et al. |

OTHER PUBLICATIONS

Bullock, A. et al., The Effect of Induced Biphasic Pulsed Currents on Re-Epithelialization of a Novel Wound Healing Model, Bioelectromagnetics vol. 28 No. 1, Jan. 1, 2007, pp. 31-41.

Djamgoz, M. et al., Directional Movement of Rat Prostate Cancer Cells in Direct-Current Electric Field: Involvement of Voltage-Gated Na+ Channel Activity, Journal of Cell Science 114 (14), 2001, pp. 2697-2705.

Fraser, S. et al., Voltage-Gated Sodium Channel Expression and Potentiation of Human Breast Cancer Metastasis, Clinical Cancer Research 11, Aug. 1, 2005, pp. 5381-5389.

Hart, F. et al., Keratinocyte Galvanotaxis in Combined DC and AC Electric Fields Supports an Electromechanical Transduction Sensing Mechanism, Bioelectromagnetics 34, Feb. 2013, pp. 85-94.

Song, B. et al., Application of Direct Current Electric Fields to Cells and Tissues in Vitro and Modulation of Wound Electric Field in Vivo. Nature Protocols. vol. 2 No. 6., Jun. 2007, pp. 1479-1489.

Sun, et al., Electrotaxis of lung cancer cells in ordered three-dimensional scaffolds, Biomicrofluids 6, 2012.

Vianale, G. et al., Extremely Low Frequency Electromagnetic Filed Enhances Human Keratinocyte Cell Growth and Decreases Proinflammatory Chemokine Productions. British Journal of Dermatology. vol. 158 No. 6., Jun. 2008, pp. 1189-1196.

Yan, X. et al., Lung Cancer A549 Cells Migrate Directionally in DC Electric Fields with Polarized and Activated EGFRs, Bioelectromagnetics 30, 2009, pp. 29-35.

\* cited by examiner

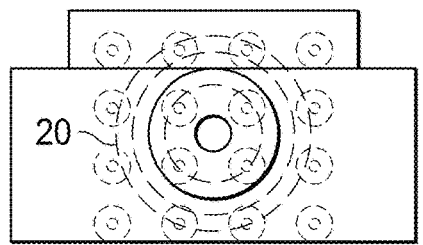 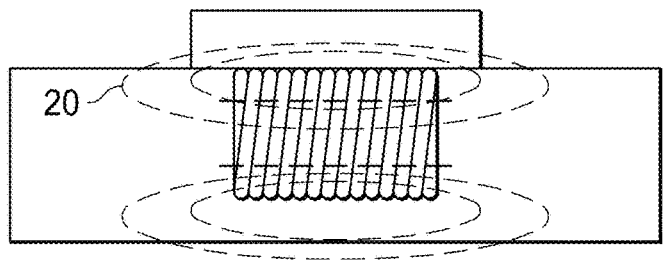
FIG. 2A  FIG. 2B
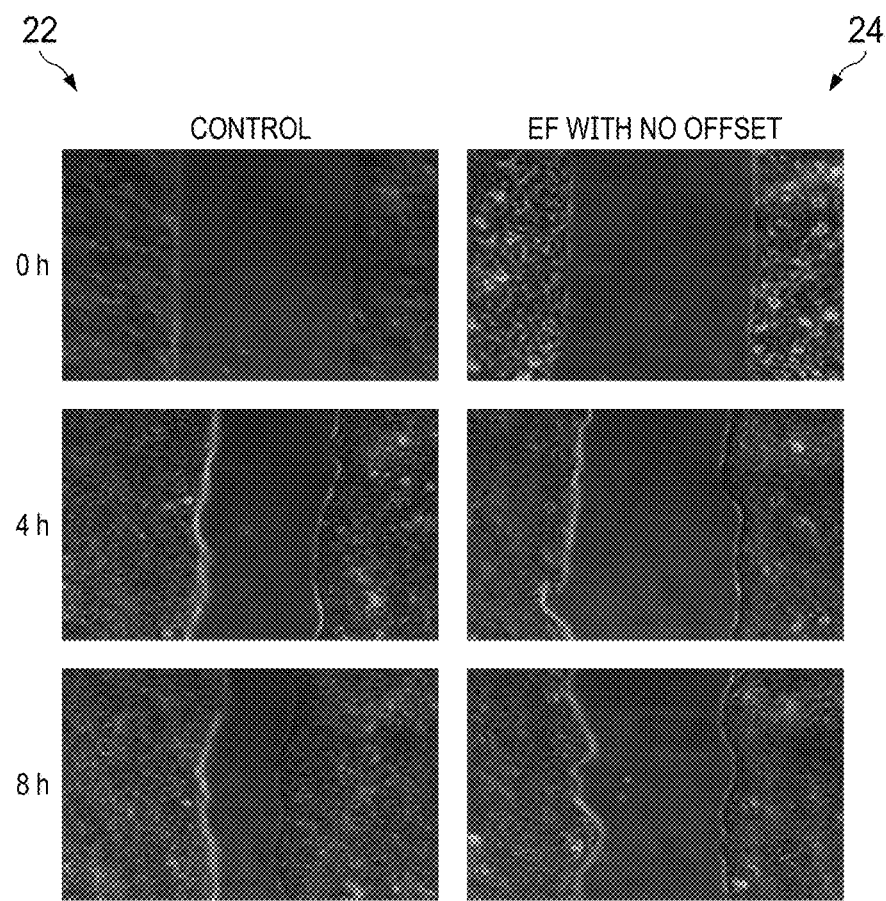
FIG. 3

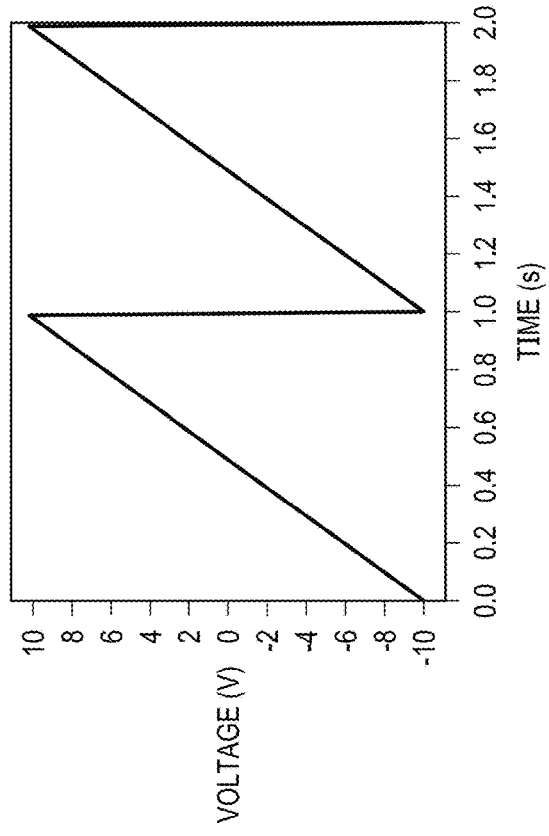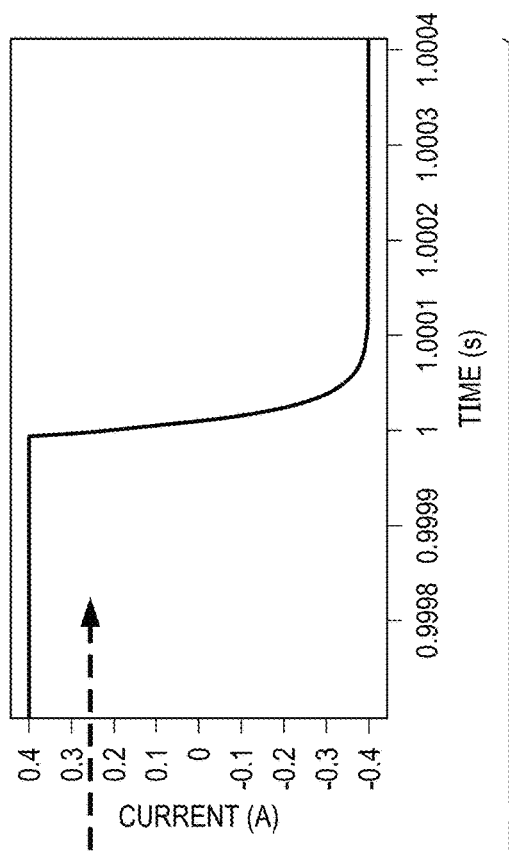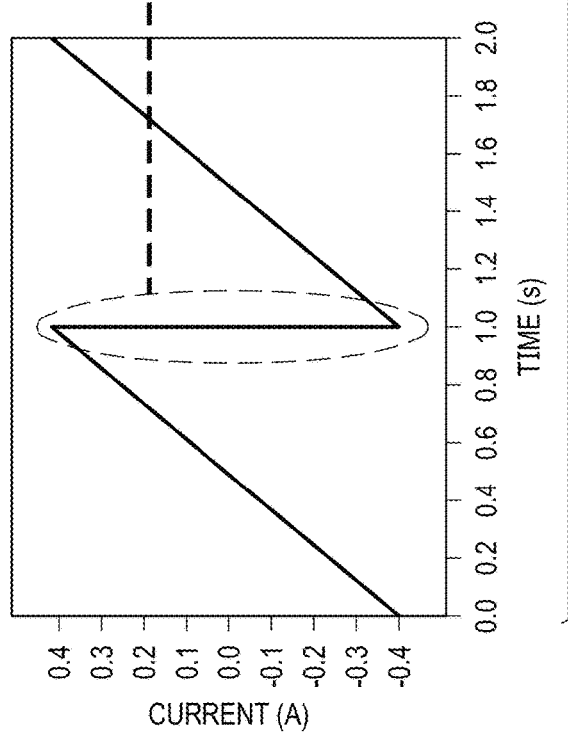
FIG. 6

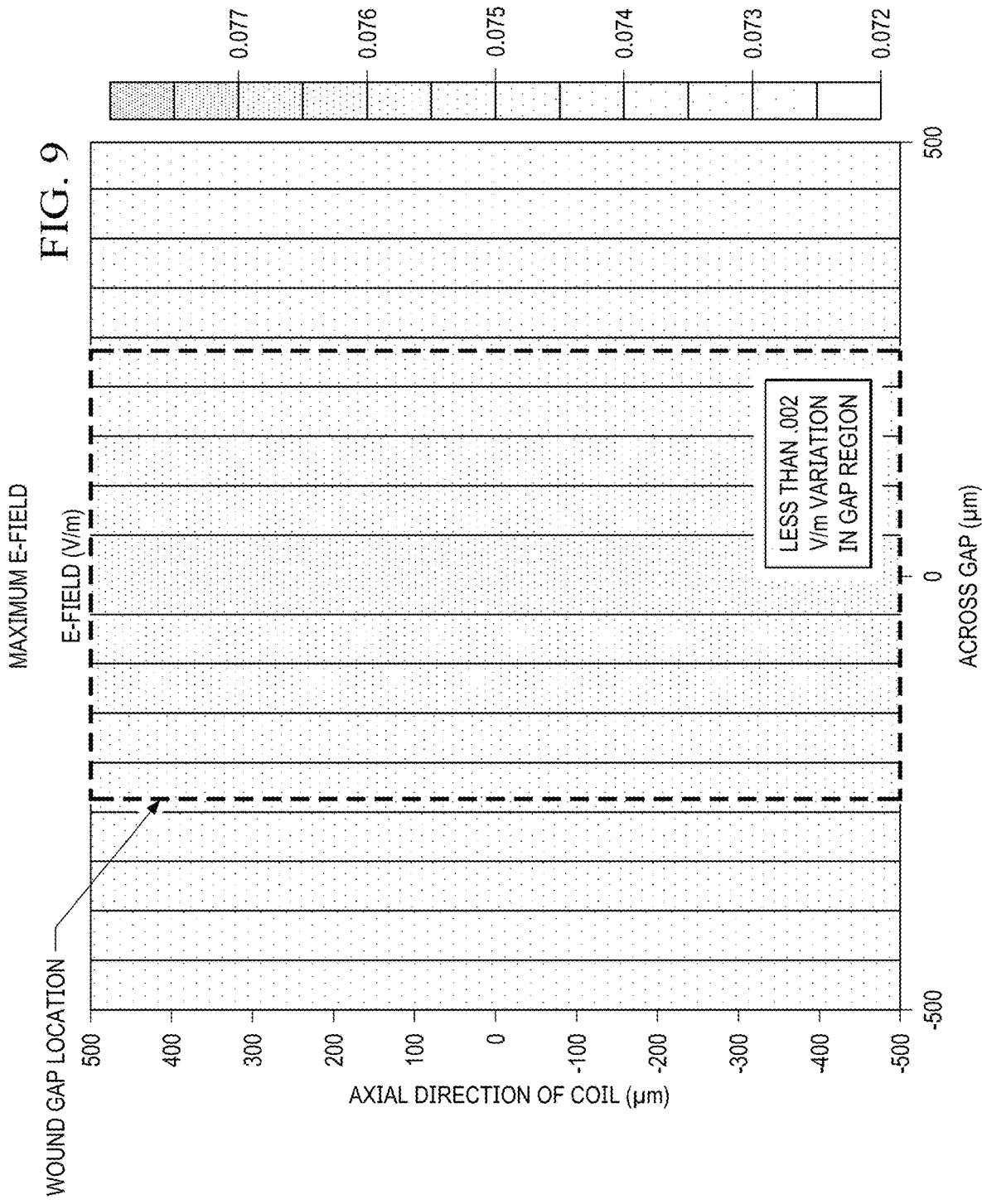

NON-CONTACT SYSTEM FOR ACCELERATING WOUND HEALING USING AN ELECTROMAGNETIC COIL TO INDUCE AN ELECTRIC FIELD TRANSVERSE TO AN AXIS OF THE WOUND

CROSS-REFERENCE TO RELATED APPLICATIONS

This application is a divisional of U.S. application Ser. No. 14/766,011, filed Aug. 5, 2015, which is a national stage entry of International Application No. PCT/US14/14782, filed Feb. 5, 2014, which claims priority to U.S. Provisional Application No. 61/760,997, filed on Feb. 5, 2013. Each of which are hereby incorporated by reference as if fully recited herein.

BACKGROUND OF THE INVENTIVE FIELD

The present invention is directed to an apparatus and method of accelerating the healing of wounds by subjecting the wound to an electric field. More particularly, the present invention is directed to an apparatus and method for accelerating the healing of a wound by applying a time-varying magnetic field to induce electric fields and eddy currents that promote healing.

There are many branches of medicine where the movement of a variety of cells occurs with beneficial effects such as in embryonic development and wound healing, and, at other times, with detrimental effects such as in cancer metastasis. It is suspected that the motility of cells in these diverse situations may be driven or be accompanied by the presence of endogenous electric fields. The directional movement of biological cells in the presence of an applied electric field is known as Galvanotaxis or electrotaxis. The effect is named after Luigi Galvani, who in the $18^{th}$ century discovered bioelectricity. The majority of experiments related to galvanotaxis over the past two centuries have involved steady electric fields applied via electrodes placed in contact with the medium containing the cells (usually, the electrodes are in contact with the medium containing the cells through agar filled tubes and the applied electric field is usually DC).

SUMMARY OF THE GENERAL INVENTIVE CONCEPT

In a preferred embodiment of the apparatus of the present invention, a time varying magnetic field from an electromagnetic (EM) coil is used to induce electric fields in a culture dish containing keratinocytes. By varying the characteristics of the excitation of the EM coil and the direction the electric field is applied, it is possible to accelerate cell migration and wound healing. In the preferred embodiment of the apparatus, the culture dish is placed on top of the cylindrical EM coil. The EM coil is connected to a function generator that generates a time varying input signal to induce a time varying electric field. The apparatus of the present invention provides a novel method to study and quantify wound healing. In one embodiment, the EM coil is driven using a function generator using a 20 Vpp, 100 kHz, sawtooth wave with a sharp ~50 ns drop to generate a rapidly time-varying magnetic field.

In an exemplary embodiment of the present invention, the method is comprised of the steps of:
providing an electromagnetic coil having a first end and a second end;
connecting the electromagnetic coil to a function generator;
applying a time-varying voltage waveform to the electromagnetic coil;
inducing a time-varying electric field around the electromagnetic coil;
placing the electromagnetic coil adjacent to the location of a wound, the wound comprised of wound cells;
orientating the placement of the electromagnetic coil to control the direction of the induced electric field;
directing the induced electric field in a direction transverse to an axis of the wound; and
controlling the migration of the wound cells using the induced electric field.

The method of the present invention induces eddy currents near the location of the wound and accelerates the healing of the wound by accelerating the migration of the wound cells using the induced electric field.

In one embodiment of the invention the time-varying waveform is a 20 volts peak to peak, 100 kHz sawtooth waveform with a 50 ns drop off at its trailing edge. The sawtooth waveform has a sharp drop on its trailing edge which induces a rapidly time-varying magnetic field.

In one embodiment of the invention, the method is further comprised of the steps of:
inducing an electric field in the direction of the surface of the wound; from below the surface of the wound; and
controlling migration of cells of different types to the surface of the wound.

The foregoing and other features and advantages of the present invention will be apparent from the following more detailed description of the particular embodiments, as illustrated in the accompanying drawings.

BRIEF DESCRIPTION OF THE DRAWINGS

The following detailed description of the example embodiments refers to the accompanying figures that form a part thereof. The detailed description provides explanations by way of exemplary embodiments. It is to be understood that other embodiments may be used having mechanical and electrical changes that incorporate the scope of the present invention without departing from the spirit of the invention.

In addition to the features mentioned above, other aspects of the present invention will be readily apparent from the following descriptions of the drawings and exemplary embodiments, wherein like reference numerals across the several views refer to identical or equivalent features, and wherein:

FIGS. 2A-B illustrate the induced electric fields produced by the EM coil of FIG. 1.

FIG. 3 illustrates microscopic images of a simulated wound from a control sample and another sample subject to an electric field.

FIG. 6 illustrates the variation of imposed voltage and drive current in the EM coil as a result of an exemplary sawtooth waveform.

FIG. 9 illustrates another view of the values of the induced electric fields in the vicinity of the simulated healing fronts for one embodiment.

DETAILED DESCRIPTION OF EXEMPLARY EMBODIMENT(S)

The present invention relates to a method for inducing electric fields in a medium containing cells by applying time-varying magnetic fields. The method uses electromagnetic (EM) induction to induce electric fields and eddy currents in the medium and galvanotaxis of cells.

Figure 1D:
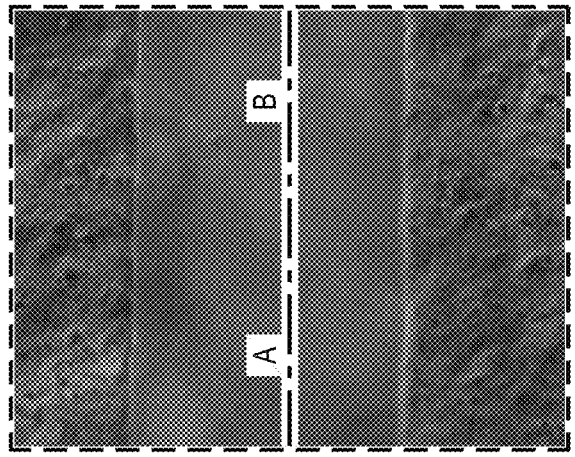
FIG. 1D illustrates a blown up image of the simulated wound in FIG. 1A.
Figure 1C:
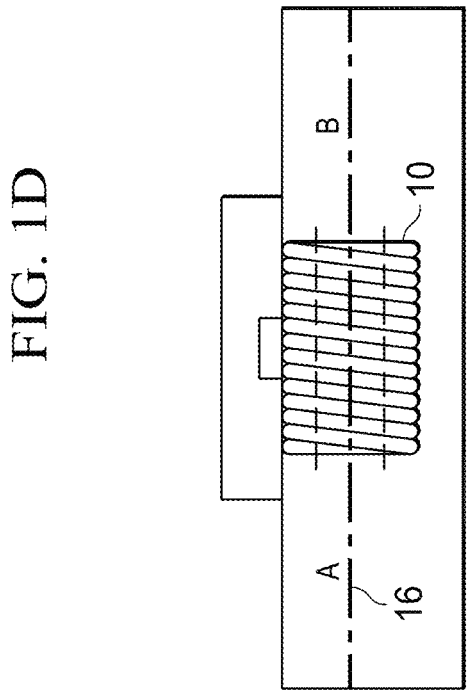
FIG. 1C illustrates a side view of one embodiment of the apparatus of the present invention.
Figure 1A:
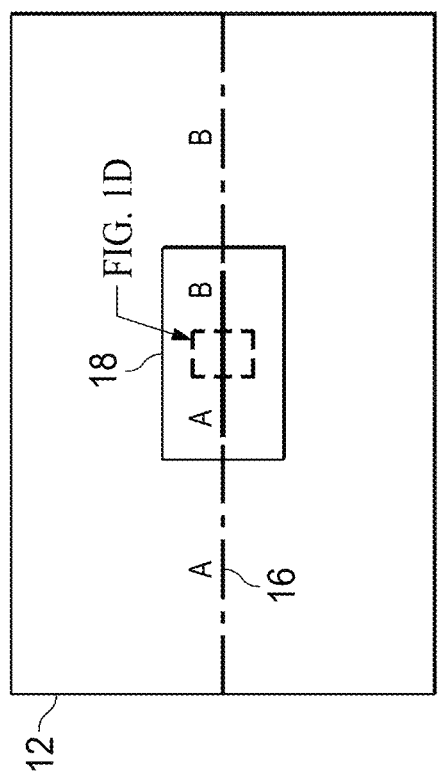
FIG. 1A illustrates a top view of one embodiment of the apparatus of the present invention.
Figure 1B:
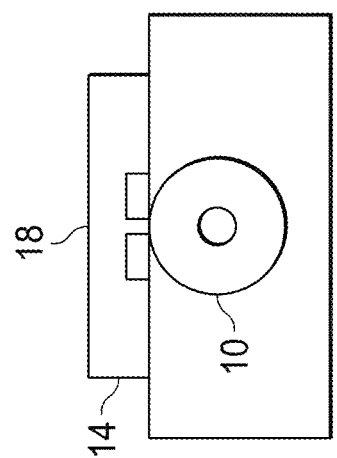
FIG. 1B illustrates a front view of one embodiment of the apparatus of the present invention.

Preliminary experiments have been conducted with human keratinocytes cultured in Dulbecco's Modified Eagle Medium (DMEM) to form a contiguous layer with a well-defined rectangular region devoid of cells so as to simulate a wound. FIG. 1 illustrates a preferred embodiment of the apparatus of the present invention. FIG. 1A is a top view, FIG. 1B is a front view, FIG. 1C is a side view and FIG. 1D illustrates a blown up image of the simulated wound in the culture plate. An EM coil 10 in a preferably cylindrical shape is placed in a holder 12. A culture plate 14 is placed on top of the EM coil (in another embodiment the culture plate can be placed to the side of the EM coil). As illustrated, in a preferred embodiment, the center line 16 of the EM coil runs in between and parallel to the gap (e.g., vacant region) that is devoid of cells (simulated wound) 18. The side view also illustrates the culture dish containing keratinocytes on top of the EM coil. The front view illustrates the culture plate on top of the EM coil as viewed from along the axis of the cylindrical coil. The top view illustrates the culture plate on top of the horizontally situated EM coil. FIG. 1D illustrates a microscope image from the top showing the region initially devoid of keratinocytes used to simulate a healing wound.

FIG. 2 illustrates the induced electric fields 20 produced by the EM coil. FIG. 2A illustrates the electric fields from a front view and FIG. 2B illustrates the electric fields from a side view. As illustrated from FIG. 2A, in the preferred embodiment, the electric field is directed transverse to the axis of the gap or wound (or along the axis of propagation of the healing front).

Normally, the initially vacant region is filled in as the cells grow inward to close the simulated wound (in about 6 to 8 hours) when placed in an incubator (at 37° C. with 5% $CO_2$). In one embodiment, the culture dish with the simulated wound is placed on an electromagnetic (EM) coil (R~22Ω, L=10 mH) situated within a fixture as shown in FIG. 1. As a control sample, a similar culture dish with the same cells and region devoid of cells (but not exposed to the EM coil) is also placed in the incubator. Both of these setups can be imaged at regular intervals over a period of 8 hours. In one embodiment, this experiment is repeated twice for a total of three runs.

In one embodiment, the EM coil is driven using a function generator using a 5 Vpp, 1 Hz sawtooth wave with a sharp ~50 ns drop to generate a rapidly time-varying magnetic field with components $B_r$ and $B_z$. In another embodiment, a 20 Vpp, 100 kHz, sawtooth wave with a sharp ~50 ns drop is used. By Faraday's law these temporally varying magnetic fields from the EM coil induce an electric field $E_\theta$ in the medium containing the cells due to the small but non-zero electrical conductivity of the medium. This component of the induced electric field $E_\theta$ has its largest component directed transverse to the axis of the simulated wound and along the axis of propagation of the healing front. At the driving frequency of 1 Hz, $E_\theta$ switches direction back and forth (left and right) along the axis of the advancing healing fronts. The magnitude of $E_\theta$ in one direction is larger than in the other because of the asymmetric sawtooth waveform imposed on the EM coil. In one embodiment, the cells are exposed to the electric field for 50 ns per second. The duration of this field remains 50 ns because of the characteristic of the sawtooth waveform but the overall duration can be increased by increasing the duty cycle (frequency on the function generator) from 1 Hz to 100 kHz.

Figure 4:
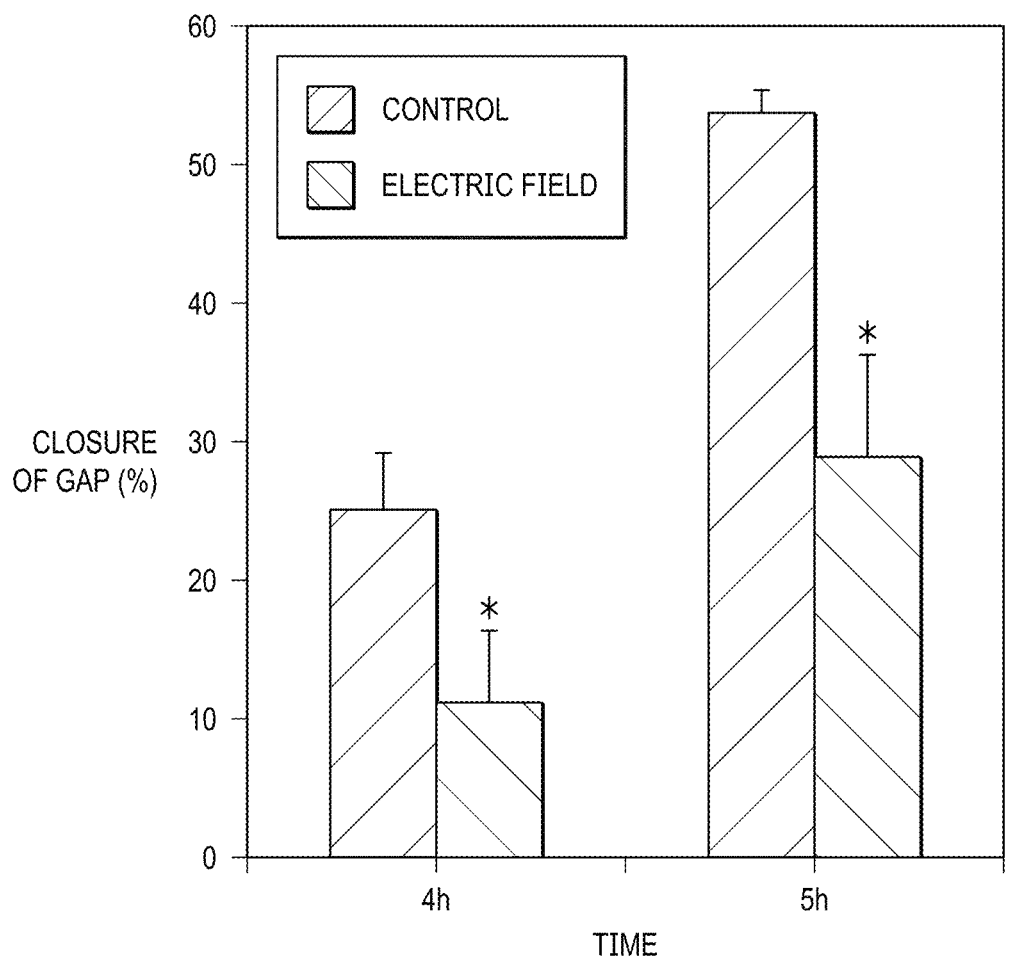
FIG. 4 illustrates quantitative measurements taken from FIG. 3.
Figure 5:
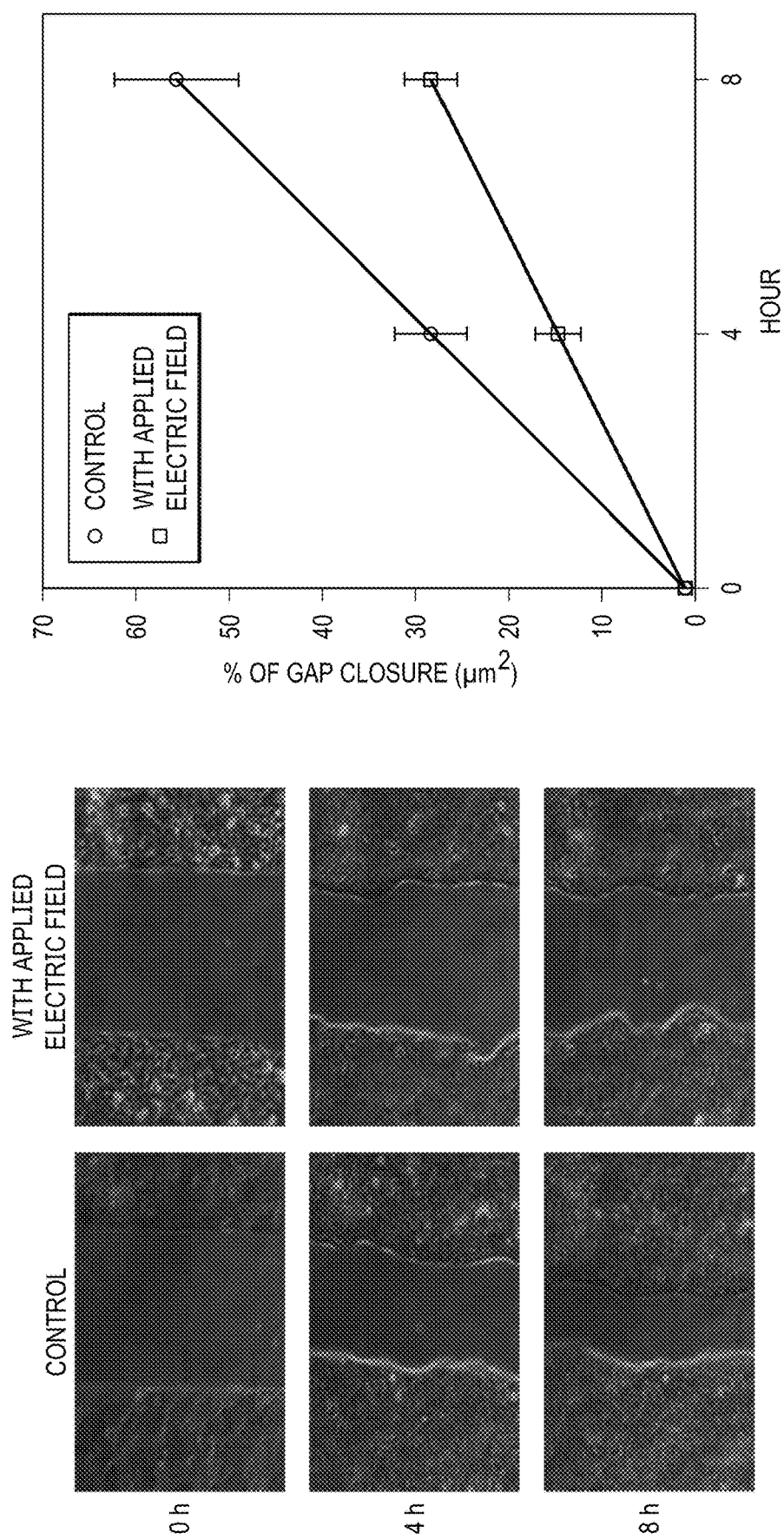
FIG. 5 illustrates another quantitative measurement taken based on percentage of gap closure.

FIG. 3 shows microscope images of the simulated wound in the control sample 22 as well as the sample subjected to the EM field 24 (images shown for 0-8 hours (h)). As illustrated, the time-varying magnetic field resulted in induced electric fields which in this geometry inhibited the advance (hence healing) of the simulated wound as can be seen in FIGS. 3-5. In contrast, the control cases (with no applied electric field) resulted in the typically observed advance of the healing fronts. Quantitative measurements from the microscope images are shown in FIG. 4 and are consistent with the qualitative information that can be gleaned from the observations shown in FIG. 3 (the data shown is for n=3 and p<0.005). Although inhibition of healing is undesirable, what is of significance is that there is a noticeable and dramatic effect because of the application of the EM field. By selecting a different set of characteristics for the driving waveform (e.g. waveform type, peak to peak, voltage, and frequency) and direction of the induced electric field (e.g. rotating $E_\theta$ in the plane of the wound) it is possible to accelerate healing (i.e. advancement of the healing fronts) shown in FIG. 3.

Figure 7:
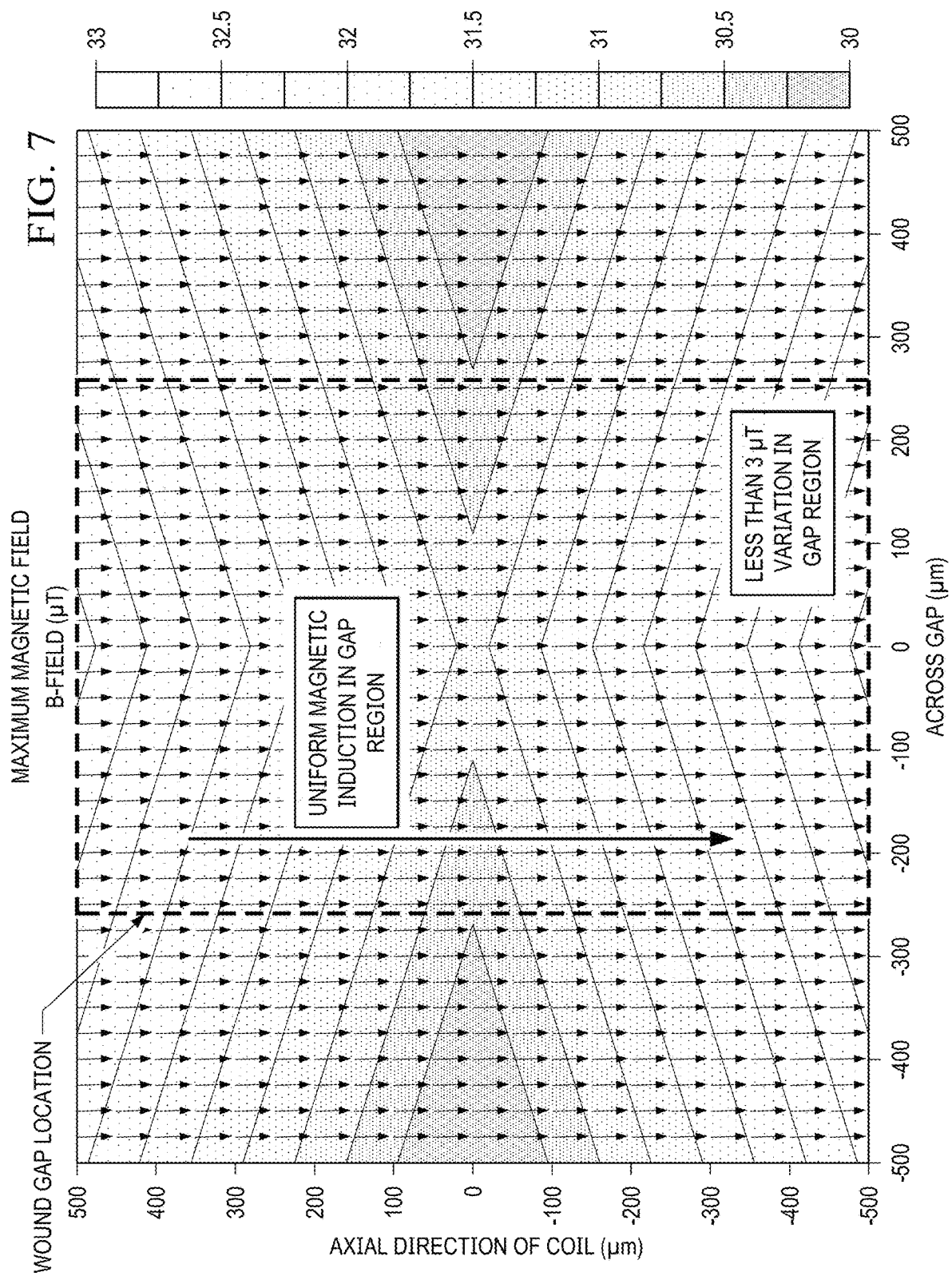
FIG. 7 illustrates calculated values of the magnetic field in the vicinity of the simulated wound for one embodiment.
Figure 8:
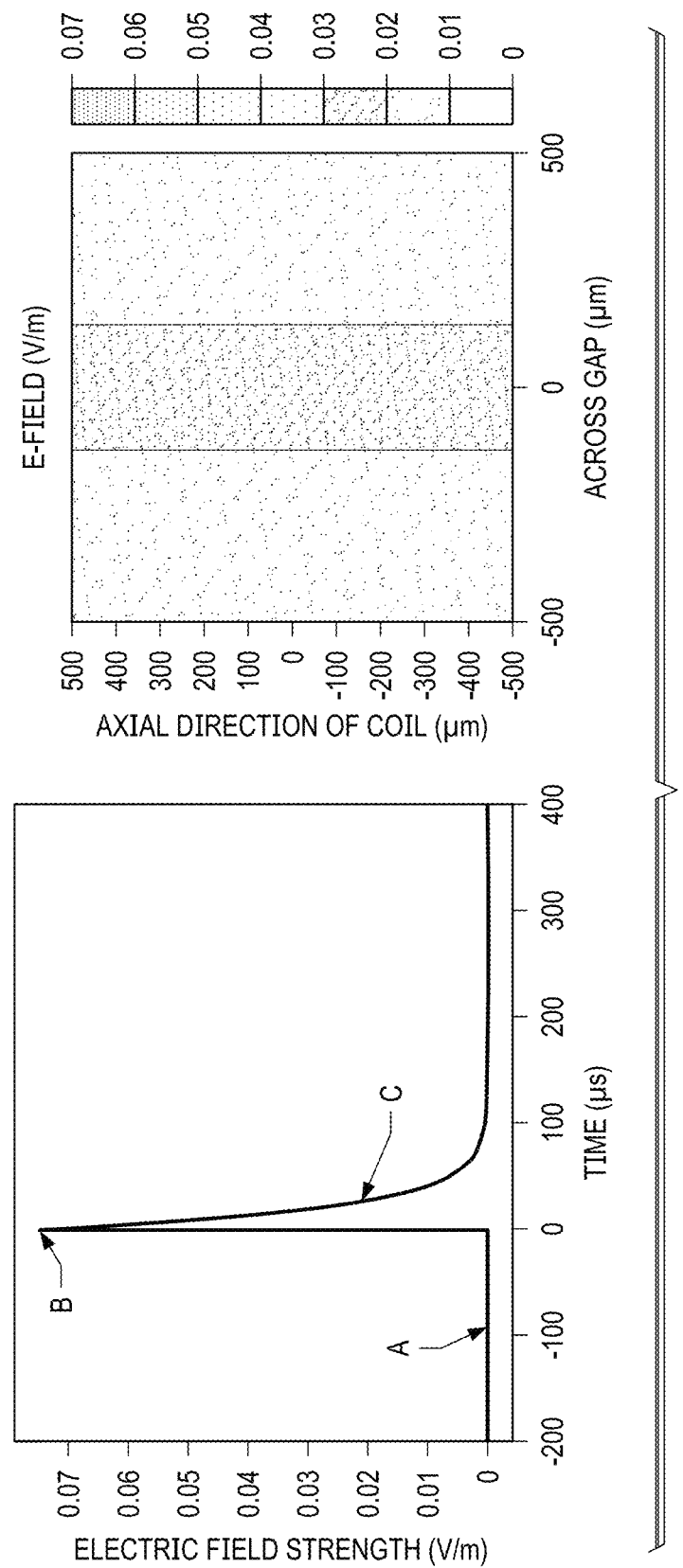
FIG. 8 illustrates the calculated values of the induced electric field in the vicinity of the simulated healing fronts for one embodiment.

Real chronic wounds are three dimensional (generally round) and not two-dimensional (or rectangular) as in the case of the assay shown in FIG. 3. Therefore, the other components of $E_\theta$, i.e., those that are not parallel to the direction of the healing front, can be used to entice different cell types (fibroblasts, immune cells, etc.) to be brought to the surface of a wound from below. Rotating the coil or inducing a rotating $E_\theta$, thereby varying the direction of the induced electric field in the plane of the wound, can also be used to accelerate rather than inhibit the healing fronts. Designing the holder and changing the position of the coil relative to the simulated wound can be used to produce an inhomogeneous $E_\theta$ so that its effects are felt only on one side of the healing front or one of the healing fronts. It should be noted this result is of significance for cancer treatment where inhibition of metastasis in tumors may have beneficial effects. FIG. 6 shows the variation of imposed voltage and driven current in the EM coil as a result of the imposed sawtooth waveform. As can be seen in the figure, the asymmetric (in time) nature of the sawtooth generates a rapidly time-varying magnetic field as the imposed voltage falls within a time span of ~50 ns. Consequently, the magnitude of the induced electric field $E_\theta$ is smaller during the rising portion (~1 s for 1 Hz excitation) and much larger for the falling portion (~50 ns). FIG. 7 shows the calculated values of the magnetic field in the vicinity of the simulated wound. As illustrated, the maximum B field is on the order of 30 µT. FIGS. 8 and 9 show the calculated values of the induced electric field $E_\theta$ in the vicinity of the simulated healing fronts. As illustrated, the maximum $E_\theta$ is on the order of 0.7 mV/cm, three orders of magnitude smaller than what is reported in traditional electrotaxis or galvanotaxis experiments. This is of significance since it demonstrates the potential for improvement in the effects discussed here by increasing the magnitude of the induced electric field by increasing the current in the EM coil.

Figure 10A:
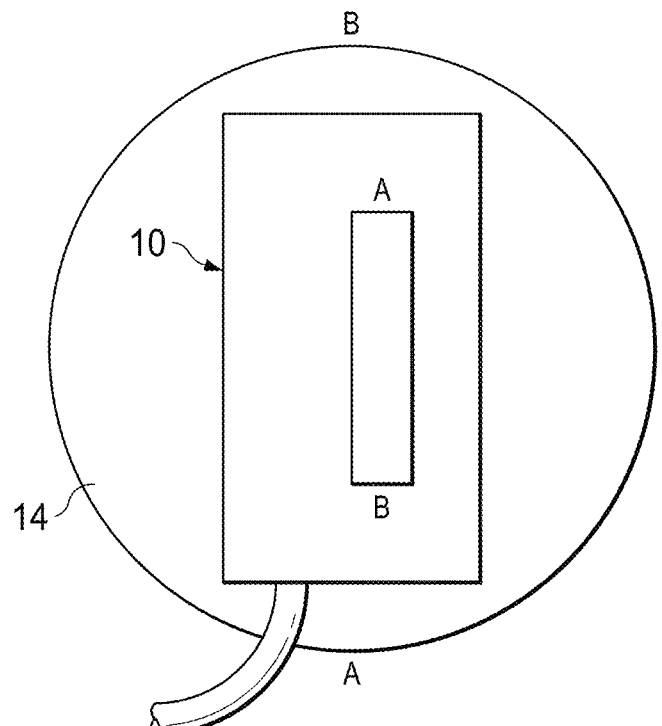
FIGS. 10A-B illustrates how the culture dish or coil can be moved with respect to each other to change the orientation or direction of the induced electric field on the simulated wound.
Figure 10B:
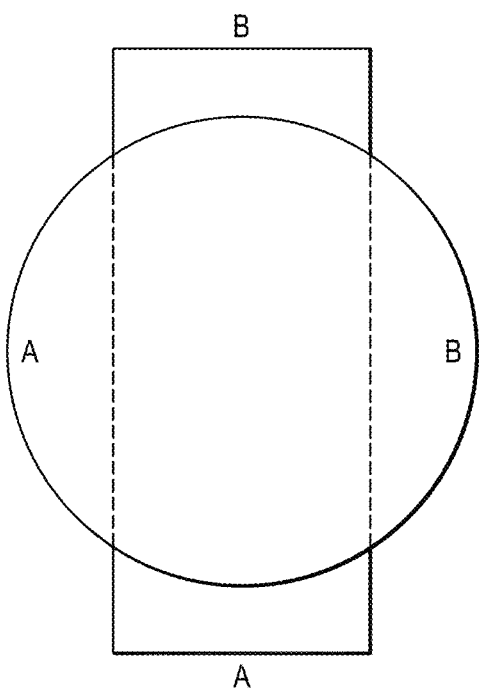

In summary, a time-varying magnetic field from an electromagnetic (EM) coil has been used to induce electric fields in a medium containing human keratinocytes and simulating a wound. In vitro measurements on a simulated wound in a contiguous layer of keratinocytes have shown that closing of the initially introduced gap can be inhibited (i.e. healing is retarded) significantly compared to control experiments where no EM field is applied. It is appreciated that directional effects due to the induced electric field causes asymmetric advancement of the wound front. By varying the characteristics of the excitation of the EM coil, and positioning of the coil relative to the wound, it is possible to accelerate wound healing. The cells remain in a contiguous layer (i.e., cells or groups of cells do not move into the gap). For example, FIGS. 10A-B illustrate how the culture dish or coil can be moved with respect to each other to change the orientation or direction of the induced electric field on the simulated wound. In other words, rotating the orientation of the culture dish or coil effectively rotates the direction of $E_\theta$.

It is possible to introduce a D.C. offset to the voltage imposed on the EM coil. However, it can be shown below that while this offset can increase the steady D.C. current in the EM coil, it does not increase $E_\theta$, (because by Faraday's law, a time-varying magnetic field is necessary). For example, an offset voltage of $V_0$ is imposed on a sinusoidally varying voltage imposed on the coil: $V_p = V_0 + V_1 \sin(\omega t)$. Then, the resulting current flowing through the coil can be calculated to be (for long times):

$$I_p(t) = \frac{V_0}{R_p} + \frac{R_p V_1 \sin(\omega t) - \omega V_1 L_p \cos(\omega t)}{(\omega^2 L_p^2 + R_p^2)}$$

The induced electric field which drives eddy currents can then be approximately determined as:

$$E_{induced} \Box \frac{\mu_0}{4\pi} \frac{dI_p}{dt} = -\frac{\mu_0}{4\pi} \left[ \frac{R_p V_1 \omega \cos(\omega t) + \omega^2 V_1 L_p \sin(\omega t)}{(\omega^2 L_p^2 + R_p^2)} \right]$$

It can be seen that the offset $V_0$ disappears. It is appreciated from the above expression for the induced electric field, that the asymmetric (in time) AC excitation of the coil should produce a time varying induced electric field and drive eddy currents that are largest in one direction.

In another embodiment of the invention, a remotely placed EM source is configured to beam an EM field to induce an electric field at the wound site (e.g., remote induction scheme). In one example, a transmitting power source placed on the ceiling or wall of a hospital room beams an EM wave to a receiving coil placed in the vicinity of a wound. Alternatively it may be possible to transmit an EM wave focused on the wound such that electric fields are induced in the desired directions.

While certain embodiments of the present invention are described in detail above, the scope of the invention is not to be considered limited by such disclosure, and modifications are possible without departing from the spirit of the invention as evidenced by the following claims:

What is claimed is:

1. A system for controlling cell migration comprised of:
    a waveform generator;
    a culture plate;
    an electromagnetic coil operably connected to the waveform generator and placed adjacent to the culture plate, the electromagnetic coil having a first end and a second end and wherein the electromagnetic coil induces an electric field when a waveform is applied to the electromagnetic coil by the waveform generator;
    keratinocytes placed in the culture plate,
    a region between the keratinocytes devoid of keratinocytes, the region having a longitudinal axis;
    wherein a center line of the electromagnetic coil runs parallel to the longitudinal axis of the region between the keratinocytes;
    wherein the waveform induces an electric field in a direction transverse to the longitudinal axis of the region between the keratinocytes; and
    directing the induced electric field along an axis of cell migration; and
    controlling the migration of cells using the induced electric field.

2. A system for controlling cell migration according to claim 1, further comprising:
    a holder for holding the electromagnetic coil; and
    wherein the holder is adapted to support the culture plate over the electromagnetic coil, and wherein the electromagnetic coil is adapted to rotate.

3. A system for controlling cell migration according to any one of claims 1 and 2, further comprising:
    an imaging device for obtaining images of the region between the keratinocytes devoid of keratinocytes for quantifying cell migration.

4. A system for controlling metastasis according to any one of claims 1 and 2, further comprising:
    a time-varying signal applied to the electromagnetic coil for inducing a time-varying electric field.

5. A system according to claim 1, wherein the waveform is a sawtooth waveform.

6. A system according to claim 1, wherein the waveform is a 20 volts peak to peak, 100 Khz sawtooth waveform with a 50 ns drop off at its trailing edge.

7. A system according to claim 1, wherein the waveform drops at the trailing edge of the waveform and wherein the induced electric field is a time-varying magnetic field.

* * * * *